United States Patent [19]
Umezawa et al.

[11] 4,455,419
[45] Jun. 19, 1984

[54] 2'-MODIFIED KANAMYCINS AND PRODUCTION THEREOF

[75] Inventors: Hamao Umezawa; Sumio Umezawa, both of Tokyo; Yoshiharu Ishido, Chofu; Shunzo Fukatsu, Tokyo, all of Japan

[73] Assignee: Zaidan Hojin Biseibutsu Kagaku Kenkyu Kai, Tokyo, Japan

[21] Appl. No.: 398,838

[22] Filed: Jul. 16, 1982

[30] Foreign Application Priority Data

Jul. 22, 1981 [JP] Japan ................................ 56-113578

[51] Int. Cl.³ ............................................ C07H 15/22
[52] U.S. Cl. .................................. 536/13.8; 424/180; 536/13.7
[58] Field of Search ............................... 536/13.7, 13.8

[56] References Cited

U.S. PATENT DOCUMENTS 3,868,360  2/1975  Daniels et al. ...................... 536/13.7
4,078,138  3/1978  Akita et al. ......................... 536/13.7
4,171,356  10/1979 Wright et al. ....................... 536/13.7
4,349,666  9/1982  Umezawa et al. .................. 536/13.7

Primary Examiner—Johnnie R. Brown
Attorney, Agent, or Firm—Larson and Taylor

[57] ABSTRACT

2'-Modified kanamycins, including 2'-deoxykanamycin A, 2'-epikanamycin A and 2'-epikanamycin B, as new compounds are produced starting from kanamycin A by consecutive reaction steps. These new compounds are useful as antibacterial agent.

9 Claims, No Drawings

2'-MODIFIED KANAMYCINS AND PRODUCTION THEREOF

SUMMARY OF THE INVENTION

This invention relates to 2'-modified kanamycin derivatives which are each a new compound useful as semisynthetic antibiotics. This invention also relates to processes for the production of these new 2'-modified kanamycin derivatives, as well as to the uses of these 2'-modified kanamycin derivatives as antibacterial agents. The new 2'-modified kanamycin derivatives according to this invention include 2'-deoxykanamycin A, 2'-epikanamycin A and 2'-epikanamycin B as well as a pharmaceutically acceptable acid-addition salt thereof.

BACKGROUND OF THE INVENTION

Many researches have been made on various derivatives of kanamycin A and kanamycin B, but the kanamycin derivatives which were synthetized in the past are limited almost to those obtained by modification of the 3'-hydroxyl group, 4'-hydroxyl group, 1-amino group and/or 6'-amino group of kanamycins, as disclosed e.g. in Japanese patent publication No. 7595/75 or the corresponding U.S. Pat. No. 3,753,973; Japanese patent application pre-publication "Kokai" No. 80038/74; U.S. Pat. No. 3,929,761; U.S. Pat. No. 3,929,762; Japanese patent publication No. 12039/80; U.S. Pat. No. 3,948,882; U.S. Pat. No. 3,939,143; U.S. Pat. No. 4,170,642 and other. This is mainly because the previous researches were made on the basis of the findings that resistant strains of bacteria have their mechanism of resistance against the aminoglycosidic antibiotics owing to their production of the various inactivating enzymes which would attack the 3'-hydroxyl group, 4'-hydroxyl group, 3-amino group, 2''-hydroxyl group and/or 6'-amino group of the aminoglycosidic antibiotics. The previous researches have succeeded to provide different derivatives of the kanamycins which are actually useful in therapeutic treatment of bacterial infections. The problem of semi-synthetizing the 2'-modified derivatives of kanamycins has been discussed and studied in recent years, but it has been found that chemical modification is difficult to be effected preferentially at the 2'-position of kanamycins. Accordingly, the intended 2'-modified derivatives of kanamycins actually have never been obtained.

We, the present inventors, attempted to effect the chemical modification at the 2'-position of kanamycins. As a result of our continued researches, we have now succeeded to achieve the preferential, chemical modification of the 2'-position of kanamycins and actually to synthetize 2'-deoxykanamycin A, 2'-epikanamycin A and 2'-epikanamycin B as the new compounds. These 2'-modified kanamycin derivatives are found to exhibit a high antibacterial activity, so that they are useful in therapeutic treatment of various bacterial infections by gram-positive bacteria and by gram-negative bacteria.

DETAILED DESCRIPTION OF THE INVENTION

According to a first aspect of this invention, therefore, there is provided as the new kanamycin derivatives a 2'-modified kanamycin derivative of the general formula (I)

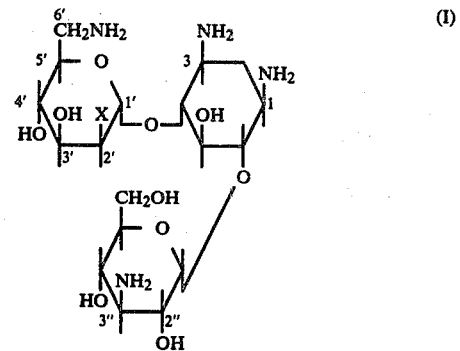

wherein X denotes a hydrogen atom, a hydroxyl group or an amino group or a pharmaceutically acceptable acid-addition salt thereof. The 2'-modified kanamycin derivative of the formula (I) according to this invention includes the compound of the formula (I) where X is the hydrogen atom (2'-deoxykanamycin A); the compound of the formula (I) where X is the hydroxyl group (2'-epikanamycin A); and the compound of the formula (I) where X is the amino group (2'-epikanamycin B).

Physico-chemical and biological properties of the 2'-modified kanamycin derivatives according to this invention are now described. 2'-Deoxykanamycin A, 2'-epikanamycin A and 2'-epikanamycin B are all in the form of a colorless and amorphous powder.

The physico-chemical properties of the new compound of this invention are summarized in Table I below.

TABLE I

| Properties | 2'-Deoxykanamycin A | 2'-Epikanamycin A | 2'-Epikanamycin B |
|---|---|---|---|
| Melting point | 208–221° C. (dec.) | 194–225° C. (dec.) | 205–220° C. (dec.) |
| Specific optical rotation | $[\alpha]_D^{25}$ + 124.8° (c: 0.9, H$_2$O) | $[\alpha]_D^{23}$ + 100.8° (c: 0.8, H$_2$O) | $[\alpha]_D^{24}$ + 105° (c: 0.5, H$_2$O) |
| $^1$H-NMR (in D$_2$O) | δ 5.46 (1H, d, J = 3.75, 1'-H) | δ 5.35 (1H, S 1'-H) | δ 5.25 (1H, S, 1'-H) |
| | δ 5.02 (1H, d, J = 3.8, 1''-H) | δ 5.25 (1H, d, J = 3.5, 1''-H) | δ 5.09 (1H, d, J = 3.5, 1''-H) |
| | δ 2.25 (1H, q, J = 4 and 10 Hz 2' equatorial-H) | δ 4.34 (1H, d, J = 3.5, 2'-H) | $^{13}$C-NMR (in D$_2$O) |
| | δ 1.72 (1H, d-t, J = 3.75 and 12 Hz, 2' axial H) | | 1'-C 103.41 ppm 2'-C 54.85 ppm |
| | | | $^{13}$C-NMR (PD = 8.5) 1'-C 101.09 ppm 2'-C 54.40 ppm |

Biological properties of the new compounds of this invention are described with reference to Table II below which shows the antibacterial spectra of the new compounds of this invention against various bacteria. The antibacterial spectra of Table II exhibit the minimum concentrations (mcg/ml) of the new compounds of this invention inhibitory to the growth of various bacteria which are estimated according to a standard serial dilution method with the estimation being made after incubation of the bacteria in nutrient agar medium at 37° C. for 24 hours.

For comparison purpose, the minimum inhibitory concentrations (mcg/ml) of the parent compound, kanamycin A are also shown in Table II.

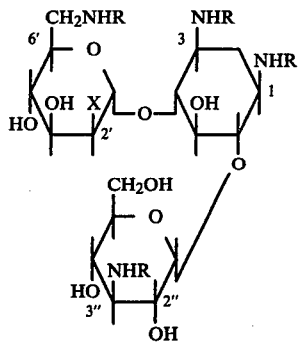

(II)

TABLE II

| Test Organisms | Minimum Inhibitory Concentrations (mcg/ml) | | | |
| --- | --- | --- | --- | --- |
| | 2'-Deoxy-kanamycin A | 2'-Epi-kanamycin A | 2'-Epi-kanamycin B | Kanamycin A (comparative) |
| *Staphylococcus aureus* Rosenbach FDA 209-OJC-1 | 0.05 | 0.39 | 1.56 | 0.10 |
| *Staphylococcus epidermidis* 109 | 0.20 | 25 | 50 | 3.13 |
| *Escherichia coli* No. 29 | 0.39 | 6.25 | 50 | 0.78 |
| *Escherichia coli* JR66/W677 (A-20683) | 50 | >100 | >100 | >100 |
| *Salmonela typhimlium* LT-2 | 0.78 | 6.25 | 50 | 1.56 |
| *Klebsiella pneumoniae* PCI-602 | 0.78 | 6.25 | 50 | 1.56 |
| *Providencia morgani* Kono | 0.78 | 6.25 | 50 | 3.13 |
| *Serratia marcescens* No. 1 | 0.78 | 12.5 | 100 | 3.13 |
| *Pseudomonas aeruginosa* IAM-1007 | 1.56 | 50 | >100 | 12.5 |
| *Pseudomonas aeruginosa* E-2 IAM-1007 | 6.25 | >100 | >100 | 50 |

For estimation of acute toxicity of the new compounds of this invention, the new compounds are each intravenously injected into mice at different dosages, from which it has been revealed that the new compounds of this invention all exhibit an $LD_{50}$ value of not less than 100 mg/kg upon intravenous injection in mice.

The 2'-modified kanamycin derivatives of this invention may form an acid-addition salt by reacting with a pharmaceutically acceptable inorganic acid such as hydrochloric acid, sulfuric acid, phosphoric acid and the like; or with a pharmaceutically acceptable organic acid such as acetic acid, propionic acid, oxalic acid, ascorbic acid and the like.

The production of the new compound of the formula (I) according to this invention is now described. Principally, the new compounds of this invention may be prepared by several reaction steps starting from kanamycin A via an intermediate 2'-O-trifluoromethylsulfonylated N,O-protected kanamycin A which is a new, intermediate product now synthetized by the present inventors. The 2'-modified kanamycin compounds of the formula (I) according to this invention may be produced in the final reaction step from the corresponding 1,3,6',3"-tetra-N-protected 2'-modified kanamycin derivative of the general formula (II)

wherein X has the same meaning as defined above and R denotes an amino-protecting group, by removing the amino-protecting groups (R) from the tetra-N-protected, 2'-modified kanamycin derivative of the formula (II) by a known N-deprotecting technique which is appropriate depending on the nature of the existing amino-protective groups (R), for example, by hydrolysis under alkaline or acidic conditions or catalytic hydrogenolysis which may be effected in a known manner in the conventional synthesis of peptides.

For easy understanding of the production of the new compounds (I) of this invention, typical procedures for the successive reaction steps to prepare the 1,3,6',3"-tetra-N-protected, 2'-modified kanamycin derivative (II) from kanamycin A are illustrated with reference to the following charts I, II, III, and IV wherein Cbe denotes an ethoxycarbonyl group as the amino-protecting group and Bz denotes a benzoyl group as the hydroxyl-protecting group.

CHART I
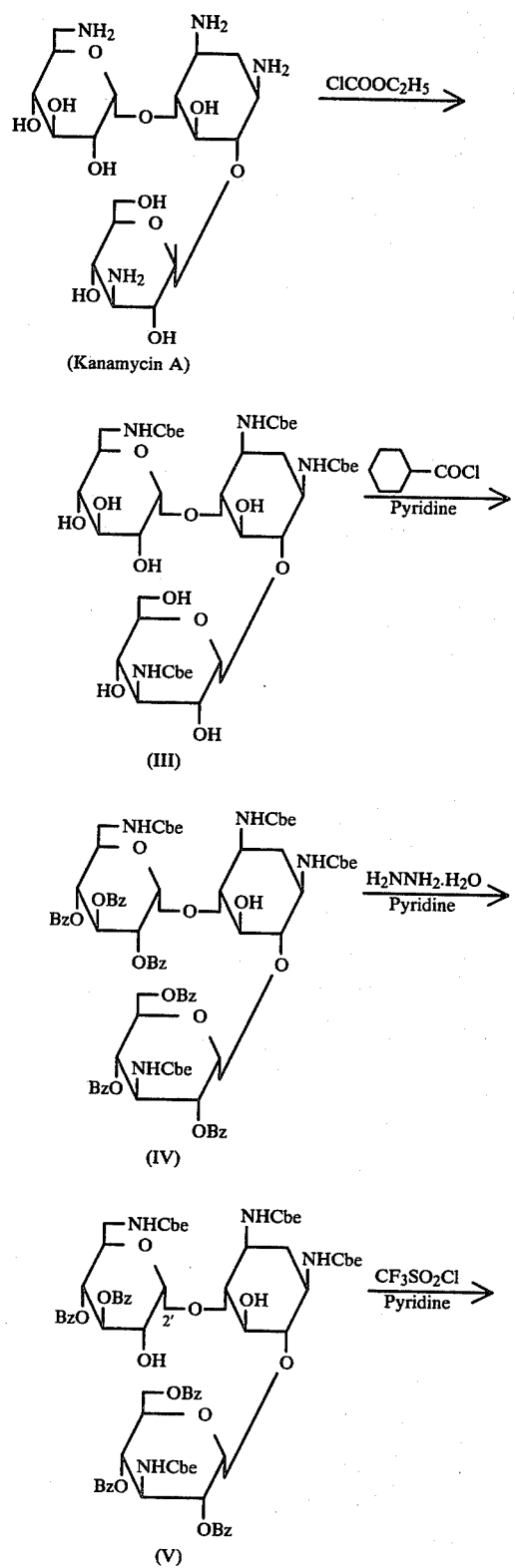
-continued
CHART I
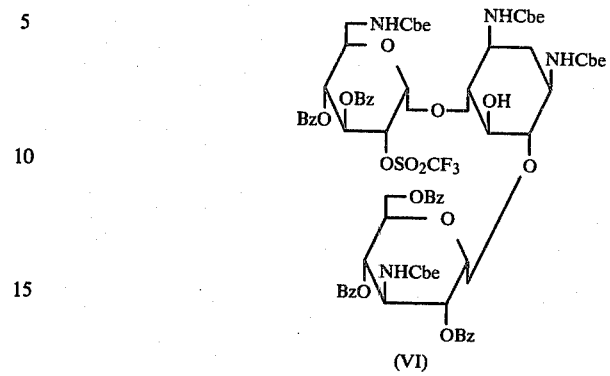
CHART II
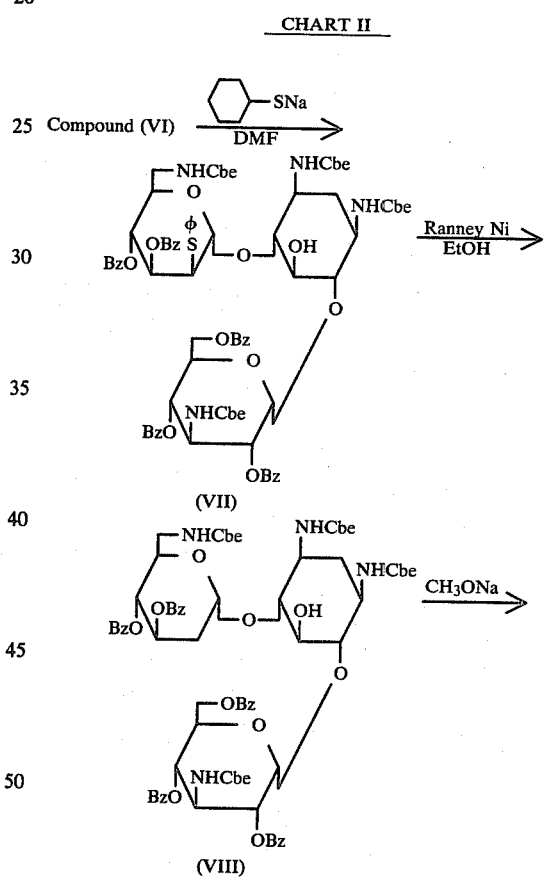
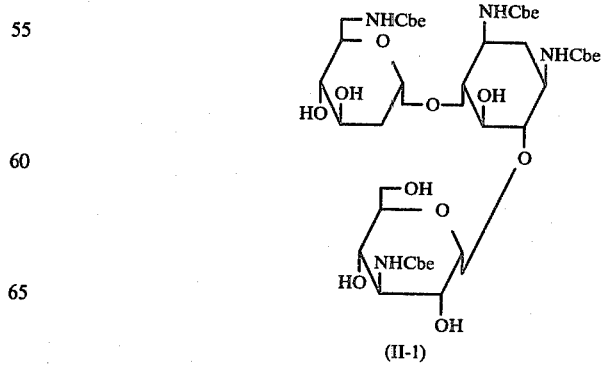

CHART III

Compound (VI) $\xrightarrow[\substack{(Y = CH_3COO- \text{ or } C_6H_5COO-, \\ M = Na \text{ or } K)}]{YM}$

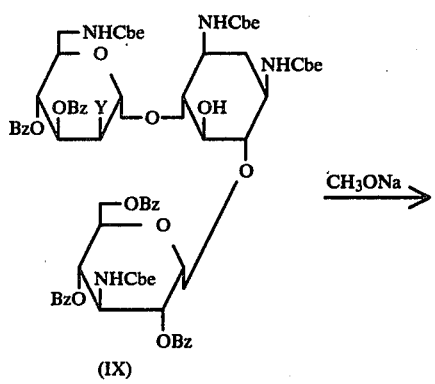

(IX)

$\xrightarrow{CH_3ONa}$

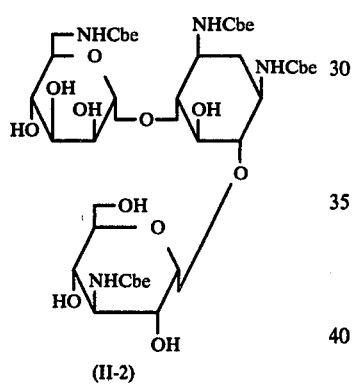

(II-2)

CHART IV

Compound (VI) $\xrightarrow{NaN_3 \text{ or } KN_3}$

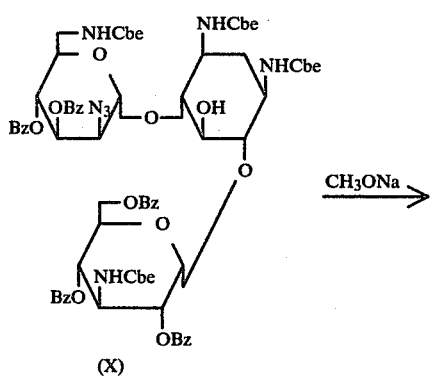

(X)

$\xrightarrow{CH_3ONa}$

-continued
CHART IV

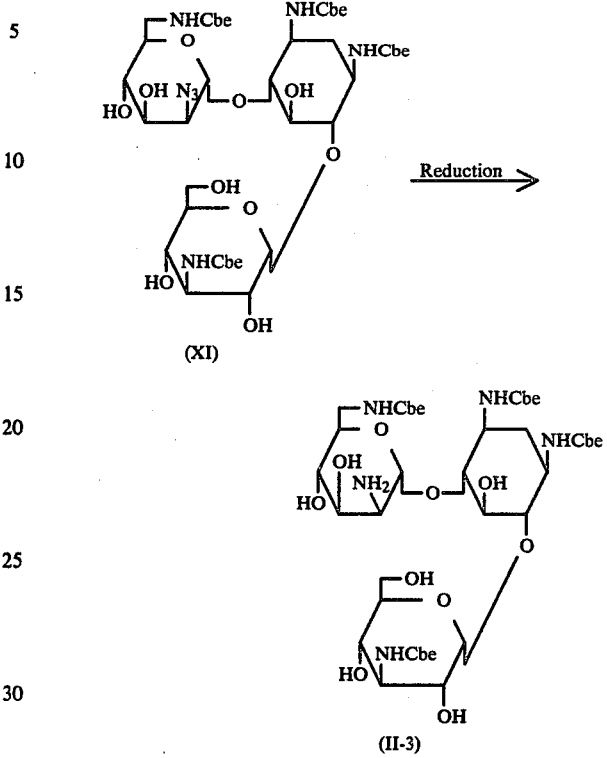

(XI)

$\xrightarrow{\text{Reduction}}$ (II-3)

With reference to Chart I, preparation of 1,3,6',3"-tetra-N-ethoxycarbonyl-2'-O-trifluoromethylsulfonyl-3',4',2",4",6"-penta-O-benzoyl-kanamycin A of the formula (VI) from kanamycin A is described.

At first, kanamycin A is used as the initial material, and all the four amino groups of kanamycin A are protected with an known amino-protecting group. In Chart I, kanamycin A is reacted with ethyl chloroformate (namely, ethoxycarbonyl chloride) in aqueous methanol to give 1,3,6',3"-tetra-N-ethoxycarbonyl-kanamycin A of the formula (III). Thus, ethoxycarbonyl group (represented by Cbe) is employed as the amino-protecting group, though the N-protection of kanamycin A may generally be achieved with anyone of the known amino-protecting groups. For instance, the N-protection of kanamycin A may be achieved with an alkoxycarbonyl group such as methoxycarbonyl, ethoxycarbonyl, butoxycarbonyl; an aralkyloxycarbonyl group such as benzyloxycarbonyl; or an aryloxycarbonyl group such as p-nitrophenyloxycarbonyl and the like. Particularly, ethyl chloroformate (for ethoxycarbonylation), benzyloxycarbonyl chloride (for benzyloxycarbonylation) or t-butoxycarbonyl chloride (for t-butoxycarbonylation, namely for introduction of t-butoxycarbonyl group, Boc) may conveniently be used as the reagent for introduction of the amino-protecting groups. The N-protection of kanamycin A may be carried out in a known manner in the conventional synthesis of peptides. However, it is preferred that kanamycin A is reacted with 4~8 molar proportions of the amino-protecting reagent in an appropriate organic solvent such as aqueous methanol or ethanol at a temperature of −10° C. to 20° C. for 10~20 hours in the presence of an alkaline agent such as sodium or potassium hydroxide, sodium or potassium hydrogen carbonate, or sodium or potassium carbonate.

Next, the tetra-N-protected kanamycin A of the formula (III) is subjected to the protection of the reactive hydroxyl groups of kanamycin A. To this end, the tetra-N-protected kanamycin A (III) is reacted with benzoyl chloride in pyridine as shown in Chart I to give 1,3,6',3''-tetra-N-ethoxycarbonyl-2',3',4',2'',6''-hexa-O-benzoyl-kanamycin A of the formula (IV). This O-benzoylation of the reactive hydroxyl groups of kanamycin A may generally be conducted by reacting the tetra-N-protected kanamycin A (III) with 6~8 molar proportions of benzoyl chloride in pyridine at a temperature of less than 10° C. overnight. Although Chart I illustrates the O-benzoylation of the tetra-N-protected kanamycin A (III) for the purpose of the O-protection to give the N,O-protected kanamycin A (IV), the desired O-protection of the tetra-N-protected kanamycin A (III) may also be achieved by acetylation with acetyl chloride. In this way, all the hydroxyl groups other than the less reactive 5-hydroxyl group of the kanamycin A can be blocked.

Then, preferential removal of the 2'-O-protecting benzoyl group from the N,O-protected kanamycin A (IV) is effected to give the 2'-O-deprotected derivative, that is, 1,3,6',3''-tetra-N-ethoxycarbonyl-3',4',2'',4'',6''-penta-O-benzoyl-kanamycin A of the formula (V). In Chart I, the 2'-O-benzoyl group is preferentially removed from the N,O-protected kanamycin A (V) by reacting the latter with hydrazine hydrate ($H_2NNH_2 \cdot H_2O$) in pyridine to give the 2'-O-deprotected kanamycin A derivative (V). The reaction for the preferential removal of the 2'-O-protecting benzoyl or acetyl group from the N,O-protected kanamycin A (IV) is a main subject of our researches in which the present inventors have been absorbed. It was firstly discovered by the present inventors that the 2'-O-protecting benzoyl or acetyl group can preferentially be removed from the N,O-protected kanamycin A (IV) by reacting the latter with 1~5 molar proportions of hydrazine hydrate, methyl hydrazine, hydroxylamine or acetate or hydrochloride thereof in an organic solvent such as pyridine, dimethylformamide, dioxane, ethanol, and mixtures of methanol and trichloromethane, at a temperature of −10° C. to 50° C. for a time of 10 to 20 hours. Thus, there is obtained the N,O-protected kanamycin A derivative of the formula (V) in which all the amino groups as well as all the reactive hydroxyl groups other than the 5- and 2'-hydroxyl groups have been protected. With this partially N,O-protected kanamycin A derivative (V) having the liberated 2'-hydroxyl group, it is feasible to make the 2'-chemical modification of kanamycin A, leading to 2'-deoxykanamycin A, 2'-epikanamycin A and 2'-epikanamycin B.

We have further found that the partially N,O-protected kanamycin A derivative of the formula (V) can preferentially be 2'-O-sulfonylated without preliminary protection of the 5-hydroxyl group when the N,O-protected kanamycin A derivative (V) is reacted with 1 molar proportion or a slight excess of trifluoromethylsulfonyl chloride ($CF_3SO_2Cl$) or trifluoromethanesulfonic anhydride as the trifluoromethanesulfonylating agent in pyridine at a temperature of 0° C. to 30° C. for a time of 20 minutes to 3 hours. Thus, in Chart I, the partially N,O-protected kanamycin A derivative (V) is reacted with trifluoromethylsulfonyl chloride in pyridine to give the 1,3,6',3''-tetra-N-ethoxycarbonyl-2'-O-trifluoromethylsulfonyl-3',4',2'',4'',6''-penta-O-benzoyl-kanamycin A of the formula (VI). This 2'-O-trifluoromethanesulfonylated kanamycin A derivative (VI) provides an important key intermediate product from which 2'-deoxykanamycin A, 2'-epikanamycin A and 2'-epikanamycin B can further be derived in different routes of reactions, respectively.

Chart II illustrates a route for the production of 2'-deoxykanamycin A from the kanamycin A 2'-O-trifluoromethanesulfonylated derivative (VI).

The kanamycin A 2'-O-trifluoromethanesulfonylated derivative (VI) is reacted with 1 molar proportion or a slight excess of sodium thiophenolate ($C_6H_5SNa$) in dimethylformamide (DMF) or other suitable organic solvent such as dioxane, acetone or tetrahydrofuran (THF) at a temperature of 10° C. to 40° C., preferably at ambient temperature for a time of 1 to 5 hours to effect the 2'-phenylthioation, giving 1,3,6',3''-tetra-N-ethoxycarbonyl-2'-deoxy-2'-epi-2'-phenylthio-3',4',2'',4'',6''-penta-O-benzoyl-kanamycin A of the formula (VII).

This 2'-epi-2'-phenylthio derivative (VII) is reacted with Ranney nickel in ethanol under refluxing to effect the removal of the 2'-phenylthio group, affording 1,3,6',3''-tetra-N-ethoxycarbonyl-2'-deoxy-3',4',2'',4'',6''-penta-O-benzoyl-kanamycin A of the formula (VIII).

The 2'-deoxykanamycin A derivative (VIII) is then treated with sodium methoxide in methanol at a temperature of 0° C. to 40° C., preferably at ambient temperature to effect the de-benzoylation, giving 1,3,6',3''-tetra-N-ethoxycarbonyl-2'-deoxykanamycin A of the formula (II-1). This N-protected 2'-deoxykanamycin A (II-1) is the N-protected 2'-modified kanamycin derivative of the general formula (II) where X is the hydrogen atom and the amino-protecting group R is ethoxycarbonyl.

Chart III illustrates a route for the production of 2'-epi-kanamycin A from the kanamycin A 2'-O-trifluoromethanesulfonylated derivative (VI).

The protected kanamycin A derivative (VI) is reacted with 1 molar proportion or a slight excess of sodium or potassium benzoate or acetate of the formula YM where Y represents a benzoxy group $C_6H_5COO$—) or acetoxy group ($CH_3COO$—) and M represents sodium or potassium atom as shown in Chart III, in an appropriate organic solvent such as dimethylformamide, dioxane, acetone, THF, at a temperature of from ambient temperature to the refluxing temperature of the solvent employed for a time of 1 to 6 hours, so that the 2'-trifluoromethylsulfonyloxy group ($—OSO_2CF_3$) is converted into 2'-epi-benzoxy or 2'-epi-acetoxy group, yielding 1,3,6',3''-tetra-N-ethoxycarbonyl-2'-O-epi-benzoyl or epi-acetyl-3',4',2'',4'',6''-penta-O-benzoyl-kanamycin A of the formula (IX). This 2'-O-epi-benzoyl or epi-acetyl kanamycin A compound (IX) is then reacted with sodium methoxide in methanol in the same manner as described in Chart II for the de-benzoylation, so that the de-acylation takes place at once at all the 2'-, 3'-, 4'-, 2''-, 4''- and 6''-positions of the kanamycin A compound, giving 1,3,6',3''-tetra-N-ethoxycarbonyl-2'-epikanamycin A of the formula (II-2). This N-protected 2'-epikanamycin A (II-2) is the N-protected 2'-modified kanamycin derivative of the general formula (II) where X is the hydroxyl group and the amino-protecting group R is ethoxycarbonyl.

Chart IV illustrates a route for the production of 2'-epikanamycin B from the kanamycin A 2'-O-trifluoromethanesulfonylated derivative (VI).

The protected kanamycin A derivative (VI) is reacted with 1 molar proportion or a slight excess of sodium or potassium azide in an organic solvent such as dimethylformamide, dioxane, acetone or THF at a temperature of from 50° C. to the refluxing temperature of the solvent employed, so that the 2'-trifluoromethylsulfonyloxy group (—OSO₂CF₃) is replaced by azido group (—N₃), affording 1,3,6',3''-tetra-N-ethoxycarbonyl-2'-deoxy-2'-epi-azido-3',4',2'',4'',6''-penta-O-benzoyl-kanamycin A of the formula (X). This 2'-epi-azido kanamycin A compound (X) is then reacted with sodium methoxide in methanol for the de-acylation (i.e., de-benzoylation) in the same manner as described in Chart II to give 1,3,6',3''-tetra-N-ethoxycarbonyl-2'-deoxy-2'-epi-azidokanamycin A of the formula (XI). This 2'-deoxy-2'-epi-azidokanamycin A compound (XI) is further catalytically hydrogenated in an appropriate organic solvent such as methanol, dioxane or THF in the presence of a known hydrogenation catalyst such as palladiumcarbon and the like to reduce the 2'-azido group (—N₃) into 2'-amino group (—NH₂). In this way, there is obtained 1,3,6',3''-tetra-N-ethoxycarbonyl-2'-epikanamycin B of the formula (II-3) which is the N-protected 2'-modified kanamycin derivative of the general formula (II) where X is the amino group and R is ethoxycarbonyl group.

The N-protected 2'-deoxykanamycin A (II-1) obtained in Chart II, the N-protected 2'-epikanamycin A (II-2) obtained in Chart III, and the N-protected 2'-epikanamycin B (II-3) obtained in Chart IV are then subjected to the conventional technique of removing the amino-protecting ethoxycarbonyl group (Cbe) therefrom, to afford the desired 2'-deoxykanamycin A, 2'-epikanamycin A and 2'-epikanamycin B, respectively.

Although the production of the N-protected 2'-modified kanamycin compounds of the formula (II-1), (II-2) or (II-3) is described above in Chart I, II, III or IV with employing the ethoxycarbonyl group as the amino-protecting group and employing the benzoyl group as the hydroxyl-protecting group, it will be clear that the known amino-protecting group other than the ethoxycarbonyl group may equally be used as stated hereinbefore as well as that the acetyl group may be used as the hydroxyl-protecting group in stead of the benzoyl group.

According to a second aspect of this invention, therefore, there is provided a process for the production of 2'-deoxykanamycin A which comprises the consecutive steps of:

(a) reacting a 1,3,6',3''-tetra-N-protected-2',3',4',2'',4'',6''-hexa-O-benzoyl or acetyl-kanamycin A of the formula (IV')

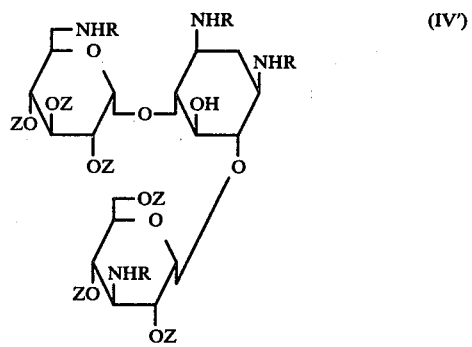

wherein R is an amino-protecting group and Z denotes a benzoyl group or acetyl group, with hydrazine, hydrazine hydrate, methyl hydrazine or hydroxylamine in pyridine at a temperature of −10° C. to 50° C. to preferentially remove the 2'-O-benzoyl or acetyl group from the compound (IV'), (b) reacting the resultant 1,3,6',3''-tetra-N-protected-3',4',2'',4'',6''-penta-O-benzoyl or acetyl-kanamycin A with trifluoromethylsulfonyl chloride or trifluoromethanesulfonic anhydride in pyridine at a temperature of 0° C. to 30° C. to give a 1,3,6',3''-tetra-N-protected-2'-O-trifluoromethylsulfonyl-3',4',2'',4'',6''-penta-O-benzoyl or acetyl-kanamycin A of the formula (VI')

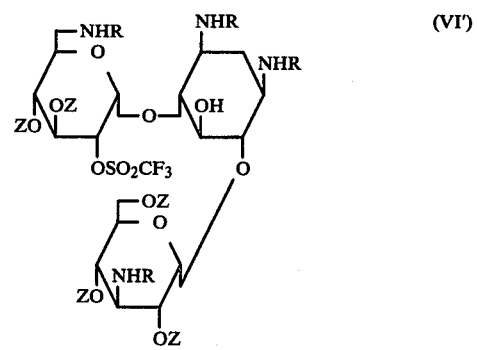

wherein R and Z are as defined above, (c) reacting the above compound (VI') with an alkali metal thiophenolate in an organic solvent at a temperature of 10° C. to 40° C. to give a 1,3,6',3''-tetra-N-protected-2'-deoxy-2'-epi-2'-phenylthio-3',4',2'',4'',6''-penta-O-benzoyl or acetyl-kanamycin A of the formula (VII')

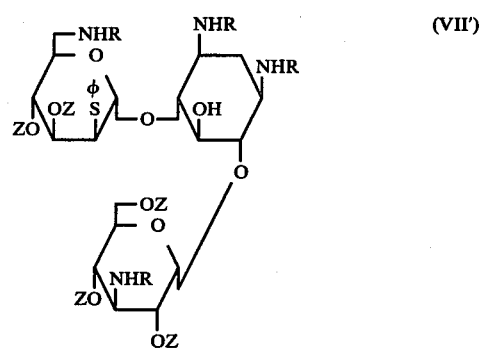

wherein R and Z are as defined above and φ denotes a phenyl group, (d) reacting the above compound (VII') with Ranney nickel in ethanol to remove the 2'-epi-2'-phenylthio group therefrom, (e) reacting the resultant 1,3,6',3''-tetra-N-protected-2'-deoxy-3',4',2'',4'',6''-penta-O-benzoyl or acetyl-kanamycin A with an alkali metal methoxide to remove the benzoyl or acetyl groups (Z) therefrom and produce the tetra-N-protected 2'-deoxykanamycin A compound of the formula (II')

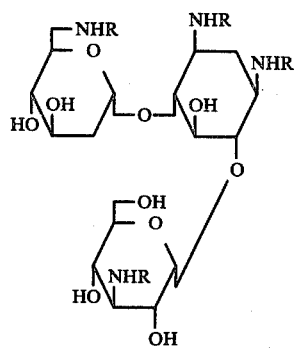

wherein R is as defined above, and (f) removing the residual amino-protecting groups (R) from the N-protected 2'-deoxykanamycin A compound (II') in a known manner to produce 2'-deoxykanamycin A.

According to a third aspect of this invention, there is provided a process for the production of 2'-epikanamycin A which comprises the consecutive steps of:

(a) reacting a 1,3,6',3''-tetra-N-protected-2',3',4',2'',4'',6''-hexa-O-benzoyl or acetyl-kanamycin A of the formula (IV')

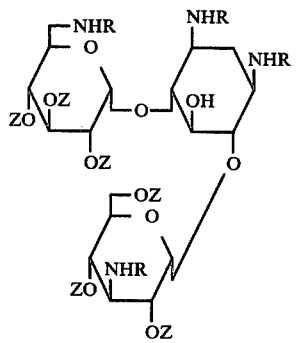

wherein R is an amino-protecting group and Z denotes a benzoyl group or acetyl group, with hydrazine, hydrazine hydrate, methyl hydrazine or hydroxylamine in pyridine at a temperature of $-10°$ C. to $50°$ C. to preferentially remove the 2'-O-benzoyl or acetyl group from the compound (IV'), (b) reacting the resultant 1,3,6',3''-tetra-N-protected-3',4',2'',4'',6''-penta-O-benzoyl or acetyl-kanamycin A with trifluoromethylsulfonyl chloride or trifluoromethanesulfonic anhydride in pyridine at a temperature of $0°$ C. to $30°$ C. to give a 1,3,6',3''-tetra-N-protected-2'-O-trifluoromethylsulfonyl-3',4',2'',4'',6''-penta-O-benzoyl or acetyl-kanamycin A of the formula (VI')

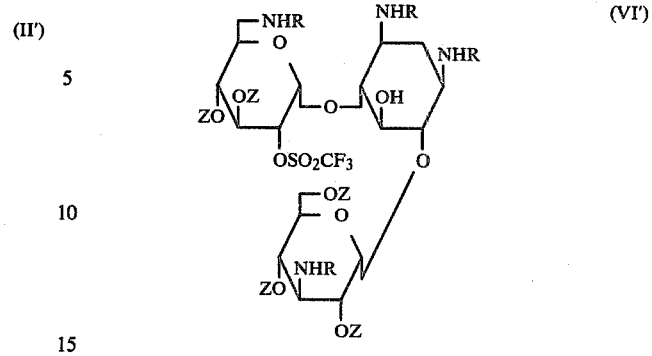

wherein R and Z are as defined above, (c) reacting the above compound (VI') with sodium or potassium benzoate or acetate in an organic solvent at a temperature of from ambient temperature to the refluxing temperature of the solvent employed, to produce a 1,3,6',3''-tetra-N-protected-2'-O-epi-benzoyl or epi-acetyl-3',4',2'',4'',6''-penta-O-benzoyl or acetyl-kanamycin A of the formula (IX')

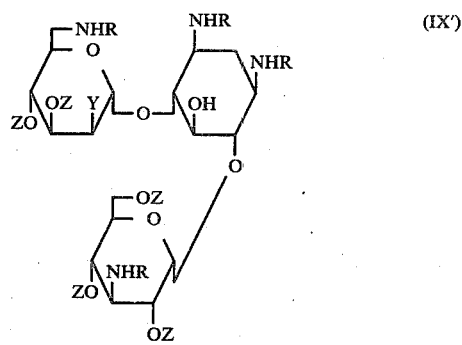

wherein R and Z are as defined above and Y denotes a benzoyl or acetyl group, (d) reacting the above compound (IX') with an alkali metal methoxide to remove the benzoyl or acetyl groups (Z and Y) therefrom and produce the tetra-N-protected 2'-epikanamycin A compound of the formula (II'')

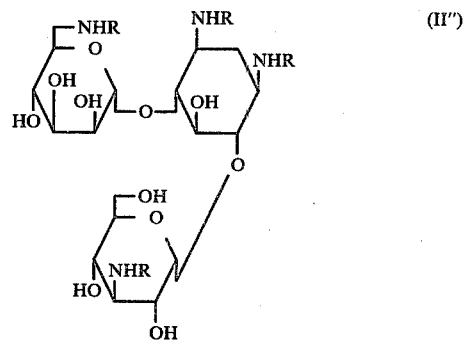

wherein R is as defined above, and (e) removing the residual amino-protecting groups (R) from the N-protected 2'-epikanamycin A compound (II'') in a known manner to produce 2'-epikanamycin A.

According to a fourth aspect of this invention, there is provided a process for the production of 2'-epikanamycin B which comprises the consecutive steps of:

(a) reacting a 1,3,6',3''-tetra-N-protected-2',3',4',2'',4'',6''-hexa-O-benzoyl or acetyl-kanamycin A of the formula (IV')

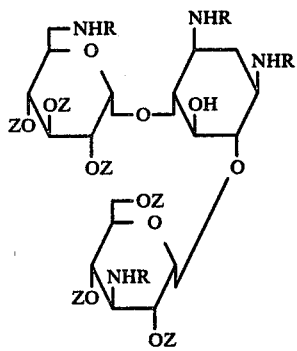

(IV')

wherein R is an amino-protecting group and Z denotes a benzoyl group or acetyl group, with hydrazine, hydrazine hydrate, methyl hydrazine or hydroxylamine in pyridine at a temperature of −10° C. to 50° C. to preferentially remove the 2'-O-benzoyl or acetyl group from the compound (IV'), (b) reacting the resultant 1,3,6',3''-tetra-N-protected-3',4',2'',4'',6''-penta-O-benzoyl or acetyl-kanamycin A with trifluoromethylsulfonyl chloride or trifluoromethanesulfonic anhydride in pyridine at a temperature of 0° C. to 30° C. to give a 1,3,6',3''-tetra-N-protected-2'-O-trifluoromethylsulfonyl-3',4',2'',4'',6''-penta-O-benzoyl or acetyl-kanamycin A of the formula (VI')

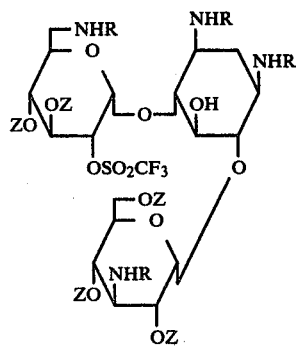

(VI')

wherein R and Z are as defined above, (c) reacting the above compound (VI') with an alkali metal azide in an organic solvent at a temperature of from 50° C. to the refluxing temperature of the solvent employed, to produce a 1,3,6',3''-tetra-N-protected-2'-deoxy-2'-epi-azido-3',4',2'',4'',6''-penta-O-benzoyl or acetyl-kanamycin A of the formula (X')

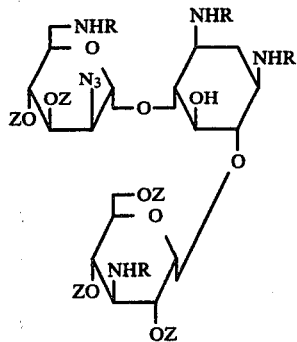

(X')

wherein R and Z are as defined above, (d) reacting the above compound (X') with an alkali metal methoxide to remove the benzoyl or acetyl groups (Z) therefrom and produce the corresponding 1,3,6',3''-tetra-N-protected-2'-deoxy-2'-epi-azido-kanamycin A of the formula (XI')

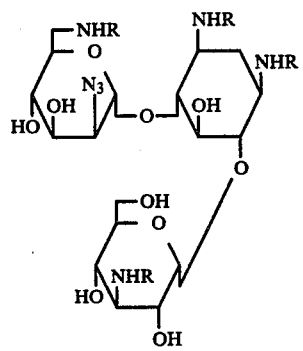

(XI')

wherein R is as defined above, (e) reducing the 2'-epi-azido group of the avove compound (XI') with hydrogen into the amino group and produce a 1,3,6',3''-tetra-N-protected-2'-epikanamycin B of the formula (II''')

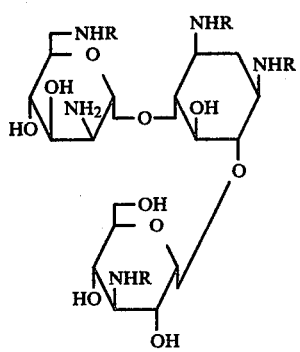

(II''')

wherein R is as defined above, and (f) removing residual amino-protecting groups (R) from the N-protected 2'-epikanamycin B compound (II''') in a known manner to produce 2'-epikanamycin B.

In carrying out the processes of the second, third and fourth aspects of this invention, the steps (a) of reacting the tetra-N-protected, hexa-O-protected kanamycin A compound (IV') with hydrazine, hydrazine hydrate or others for preferential removal of the 2'-O-benzoyl or acetyl group, as well as the step (b) of reacting the resultant 2'-O-deprotected kanamycin A compound with trifluoromethylsulfonyl chloride or trifluoromethanesulfonic anhydride for production of the N,O-protected, 2'-O-trifluoromethylsulfonyl-kanamycin A compound (VI') may be conducted in the same manner as described hereinbefore with reference to Chart I for the steps of producing the aforesaid 2'-O-deprotected kanamycin A derivative of the formula (V) and the step of producing the aforesaid 2'-O-trifluoromethylsulfonyl-kanamycin A derivative of the formula (VI), respectively.

The step (c) of reacting the compound (VI') with an alkali metal thiophenolate in the process of the second aspect of this invention may be conducted in the same manner as described with reference to Chart II for the step of reacting the kanamycin A 2'-O-trifluoromethanesulfonylated derivative (VI) with sodium thiophenolate. The alkali metal thiophenolate may be sodium or potassium thiophenolate. The steps (d) and (e) of the second aspect process of this invention may also be conducted in the same manner as described with reference to Chart II for the corresponding steps of producing the aforesaid kanamycin A derivatives of the formulae (VIII) and (II-1), respectively.

Similarly, the step (c) of reacting the compound (VI') with sodium or potassium benzoate or acetate and the step (d) of reacting the resultant product (IX') with an alkali metal methoxide according to the process of the third aspect of this invention may be effected in the same manner as described with reference to Chart III in respect of the step of producing the 2'-O-epi-benzoyl or epi-acetyl-kanamycin A derivative of the formula (IX) and the step of producing the N-protected 2'-epikanamycin A of the formula (II-2), respectively.

Equally, the steps (c) of reacting the compound (VI') with an alkali metal azide, the step (d) of reacting the resultant 2'-epi-azido-kanamycin A derivative (X') with an alkali metal methoxide, the step (e) of reducing the resultant debenzoylated or deacetylated 2'-epi-azidokanamycin A derivative (XI') according to the process of the fourth aspect of this invention may be carried out in the same way as described with reference to Chart IV in respect of the corresponding steps of producing the kanamycin A derivatives (X), (XI) and the 2'-epikanamycin B derivative (II-3), respectively.

In any way, there is prepared in the last but one step of the processes of the second, third and fourth aspects of this invention the 1,3,6',3''-tetra-N-protected derivative of 2'-deoxykanamycin A, 2'-epikanamycin A or 2'-epikanamycin B which is represented by the aforesaid formula (II'), (II'') or (II'''). In order to produce the desired 2'-deoxykanamycin A, 2'-epikanamycin A or 2'-epikanamycin B, therefore, it is necessary in the final step of the processes of this invention to remove the residual amino-protecting groups (R) from the tetra-N-protected 2'-modified kanamycin compound of the formula (II'), (II'') or (II''') which may generically be represented by the general formula (II) as shown hereinbefore.

The removal of the residual amino-protecting groups (R) can be effected by conventional N-deprotecting technique which is known in the synthesis of peptides, for instance, by alkaline hydrolysis, acidic hydrolysis or hydrogenolysis, depending on the nature of the existing amino-protecting groups. Thus, the amino-protecting group of the alkoxycarbonyl type or the aryloxycarbonyl type may be removed either by alkaline hydrolysis, preferably by heating in a saturated solution of barium hydroxide in water, aqueous 5N sodium hydroxide or aqueous 5N potassium hydroxide; or by acidic hydrolysis, preferably by treating with an acid, for example, 1N hydrochloric acid in aqueous methanol or aqueous trifluoroacetic acid at ambient temperature or at an elevated temperature. The amino-protecting group of the aralkyloxycarbonyl type such as benzyloxycarbonyl may be removed by hydrogenolysis which is effected in water or in aqueous or anhydrous organic solvent such as dioxane, methanol and the like at ambient temperature or at an elevated temperature in the presence of a known hydrogenolysis catalyst such as palladium-carbon using hydrogen gas under atmospheric, superatmospheric or subatmospheric pressure. The reaction mixture from the N-deprotection reaction may be neutralized, if desired, before the desired 2'-modified kanamycin derivative of the formula (I) is recovered therefrom. The desired 2'-modified kanamycin compound of the formula (I) may be isolated and purified chromatographically in the same manner as in the conventional technique of purifying the known water-soluble, basic antibiotics with aid of ion-exchange resins. For instance, the reaction solution containing the desired 2'-modified kanamycin derivative (I) dissolved therein may be treated with a cation-exchange resin such as Amberlite IRC-50 or Amberlite CG-50 (both are the products of Rohm & Haas Co., U.S.A.) for adsorption of the active compound and the resin may then be eluted with aqueous ammonia at different concentrations, followed either by concentration of the active fractions of the eluate to dryness, or by dry-freezing of the active fractions of the eluate. In this way, the desired new compound (I) of this invention is obtained and if desired, it may be converted into an acid-addition salt by reacting with a pharmaceutically acceptable acid in a known manner.

The new compounds of the formula (I), according to this invention and its pharmaceutically acceptable acid addition salt may be administered orally, intraperitoneally, intravenously, subcutaneously or intramuscularly using any pharmaceutical form known to the art for such administration and in a similar manner to the known kanamycins. For instance, the new compounds of this invention may be administered orally using any pharmaceutical form known to the art for oral administration. Examples of the pharmaceutical forms for oral administration are powders, capsules, tablets, syrup and the like. A suitable dose of the new compounds of this invention for effective treatment of bacterial infections is in a range of 0.1 to 1 g per person a day when it is given orally. It is preferred that said dose should be orally administered in three to four aliquots per day. The new compounds of this invention may also be administered by intramuscular injection at a dosage of 50 to 500 mg per person two to four times per day. Moreover, the new compounds of this invention may be formulated into an ointment for external application which contains the active compound at a concentration of 0.5~5% by weight in mixture with a known ointment base such as polyethylene glycol. Furthermore, the new compounds of this invention are each useful for sterilization of surgical instruments and sanitary materials.

According to a further aspect of this invention, there is provided an antibacterial composition comprising as the active ingredient 2'-deoxykanamycin A, 2'-epikanamycin A or 2'-epikanamycin B or a pharmaceutically acceptable acid-addition salt thereof in an antibacterially effective amount to combat the bacteria, in combination with a carrier for the active ingredient compound.

This invention is now illustrated with reference to the following Examples to which this invention is not limited.

EXAMPLE 1

Production of 2'-deoxykanamycin A (1) Preparation of tetra-N-ethoxycarbonylkanamycin A Kanamycin A sulfate (40 g) was dissolved in a mixture of 400 ml of 2N aqueous sodium hydroxide and 200 ml of methanol, and to the resultant solution was added dropwise 69 ml of ethyl chloroformate. The mixture obtained was stirred at ambient temperature for 4 hours and then filtered to remove the deposited solid which was then washed with water and dried to give 1,3,6',3''-tetra-N-ethoxycarbonyl-kanamycin A. Yield 45.7 g (86%).

m.p. 266° ~267° C. (dec.) $[\alpha]_D^{25}+48.3°$ (c 0.5, DMF)

Elemental analysis Calcd. for $C_{30}H_{52}N_4O_{19}$: C: 46.62, H: 6.80, N: 7.25%; Found: C: 45.92, H: 6.79, N: 7.05%.

(2) Preparation of 1,3,6',3''-tetra-N-ethoxycarbonyl-2',3',4',2'',4'',6''-hexa-O-benzoyl-kanamycin A The tetra-N-ethoxycarbonyl-kanamycin A (7.73 g) obtained in the above procedure (1) was dissolved in 200 ml of pyridine and the resultant solution was admixed with 12.2 ml of benzoyl chloride. The admixture obtained was allowed to stand at 5° C. overnight to effect the O-benzoylation. The reaction mixture was admixed with 1 ml of water and distilled under reduced pressure to remove the solvent. The residue was admixed with 300 ml of ethyl acetate and the admixture was washed with water, then with a saturated aqueous solution of sodium hydrogen carbonate and finally twice with water. The organic layer was dried over anhydrous sodium sulfate and then concentrated under reduced pressure to dryness to afford the titled compound. Yield 13.6 g (97.3%).

m.p. 195°~215° C. $[\alpha]_D^{25}+100.7°$ (c 0.9, CHCl$_3$)

Elemental analysis Calcd. for $C_{72}H_{76}N_4O_{25}$: C: 61.87, H: 5.49, N: 4.01%; Found: C: 61.78, H: 5.42, N: 3.87%.

(3) Preparation of 1,3,6',3''-tetra-N-ethoxycarbonyl-3',4',2'',4'',6''-penta-O-benzoyl-kanamycin A The tetra-N-ethoxycarbonyl-hexa-O-benzoyl-kanamycin A product (42 g) obtained in the above procedure was dissolved in 60 ml of pyridine and the resulting solution was admixed with 0.48 ml of hydrazine hydrate. The admixture obtained was allowed to stand at ambient temperature overnight to effect the reaction for preferential removal of the 2'-O-benzoyl group. The reaction mixture was admixed with 2 ml of acetone and then distilled under reduced pressure to remove the solvent therefrom. The residue was admixed with 150 ml of ethyl acetate and then washed with water, then with 1N aqueous potassium hydrogen sulfate, subsequently with a saturated aqueous solution of sodium hydrogen carbonate and finally twice with water. The organic layer was dried over anhydrous sodium sulfate and distilled under reduced pressure to remove the solvent, giving 3.8 g of a crude product of the titled compound. This crude product was purified by chromatography on silica gel (75 g) developed with chloroform-methanol (50:1) to afford the titled compound. Yield 2.6 g (67%).

m.p. 193°~202° C. $[\alpha]_D^{25}+85.5°$ (c 1.0, CHCl$_3$)

Elemental analysis Calcd. for $C_{65}H_{72}N_4O_{24}$: C: 60.35, H: 5.62, N: 4.33%; Found: C: 59.41, H: 5.51, N: 4.32%.

(4) Preparation of 1,3,6',3''-tetra-N-ethoxycarbonyl-2'-O-trifluoromethylsulfonyl-3',4',2'',4'',6''-penta-O-benzoyl-kanamycin A The tetra-N-ethoxycarbonyl-penta-O-benzoyl-kanamycin A product (2.37 g) obtained in the above procedure (3) was dissolved in 40 ml of pyridine, and the resulting solution was admixed with 0.9 g of 4-N-dimethylaminopyridine, followed by dropwise addition of 0.6 ml of trifluoromethylsulfonyl chloride thereto under ice-cooling. The liquid mixture obtained was allowed to stand at ambient temperature for 20 minutes and the reaction mixture was admixed with 0.5 ml of water and then distilled under reduced pressure to remove the solvent therefrom. The residue was admixed with 60 ml of ethyl acetate and the admixture obtained was washed with water, then with a saturated aqueous solution of sodium hydrogen carbonate, subsequently with 1N aqueous potassium hydrogen sulfate and finally with water. The organic layer was dried over anhydrous sodium sulfate and then distilled under reduced pressure to give 2.3 g of a crude product of the above titled compound. This crude material was purified by chromatography on silica gel (30 g) developed with chloroform-methanol (50:1) to afford the titled compound. Yield 2.2 g (85%).

m.p. 125°~137° C. (dec.) $[\alpha]_D^{25}+110.5°$ (c 0.7, CHCl$_3$)

IR($\nu_{KBr}$, cm$^{-1}$): 1140, 1415 (SO$_2$CF$_3$)

$^1$H-NMR (COCl$_3$): δ7.2~8.3

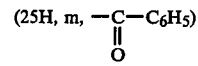

(25H, m, —C—C$_6$H$_5$)
         ‖
         O (5) Preparation of 1,3,6',3''-tetra-N-ethoxycarbonyl-2'-deoxy-2'-epi-2'-phenylthio-3',4',2'',4'',6''-penta-O-benzoyl-kanamycin A The 2'-O-trifluoromethylsulfonyl-kanamycin A compound (2.1 g) obtained in the above procedure (4) was dissolved in 30 ml of DMF (dimethylformamid) and the resultant solution was admixed with 430 mg of sodium thiophenolate. The admixture obtained was allowed to stand at ambient temperature for 3 hours to effect the reaction for introduction of the epi-2'-phenylthio group into the kanamycin A compound. The reaction mixture was distilled under reduced pressure to remove the solvent therefrom, and the residue was admixed with 60 ml of ethyl acetate, followed by washing twice with water. The organic layer was dried over anhydrous sodium sulfate and then distilled under reduced pressure to give 2.0 g of a crude solid product of the titled compound. This crude product was purified by chromatography with silica gel (30 g) developed by chloroform-methanol (50:1) to afford the above titled compound. Yield 1.8 g (88%).

m.p. 148°~165° C. $[\alpha]_D^{25}+87.7°$ (c 1.0, CHCl$_3$)

$^1$H-NMR (CDCl$_3$): δ6.8~7.0 (5H, m, s—C$_6$H$_5$) δ7.2~8.2

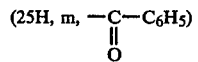

(25H, m, —C—C$_6$H$_5$)
         ‖
         O

Elemental analysis Calcd. for $C_{71}H_{76}N_4O_{23}S$: C: 61.54, H: 5.54, N, 4.04, S:2.31%; Found: C: 61.68, H: 5.50, N: 3.71, S: 2.36%.

(6) Preparation of 1,3,6',3''-tetra-N-ethoxycarbonyl-2'-deoxy-3',4',2'',4'',6''-penta-O-benzoyl-kanamycin A The 2'-phenylthio-kanamycin A derivative (1.5 g) obtained in the above procedure (5) was dissolved in 35 ml of ethanol and the resulting solution was mixed with 10 ml of Ranney nickel. The mixture obtained was heated for 30 minutes under refluxing. The reaction mixture was filtered to remove the insoluble solid therefrom, and the filtrate was concentrated to dryness to give 1.35 g of a crude product of the above titled compound. This was then purified by chromatography with silica gel (25 g) developed with chloroform-methanol (45:1), to afford 1.3 g of the titled compound. Yield 93%.

m.p. 140°~155° C. $[\alpha]_D^{25} +74°$ (c 1.0, CHCl$_3$)

Elemental analysis Calcd. for C$_{65}$H$_{72}$N$_4$O$_{23}$: C: 61.11, H: 5.69, N: 4.39%; Found: C: 61.00, H: 5.63, N 4.24%.

(7) Production of 2'-deoxykanamycin A

The N,O-protected 2'-deoxykanamycin A derivative (1.1 g) obtained in the above procedure (6) was dissolved in 30 ml of methanol, and the resulting solution was mixed with 0.7 ml of a solution of 28% sodium methoxide in methanol to adjust the mixture to pH 11, and the whole mixture was allowed to stand at ambient temperature for 30 minutes to effect the removal of the O-benzoyl groups. The reaction mixture was neutralized by addition of 1N-HCl and the neutralized solution was concentrated under reduced pressure. The concentrated solution (residue) was admixed with 3.5 g of barium hydroxide (Ba(OH)$_2$.8H$_2$O) and 50 ml of water, and the admixture was agitated and heated for 3 hours under refluxing for the N-deprotecting reaction. After allowing to cool, the reaction mixture was neutralized by passage of carbon dioxide gas therethrough and then filtered to remove the insoluble matter therefrom. The filtrate was passed through a column of a cation-exchange resin, Amberlite CG-50 (NH$_4$$^+$ form) (20 ml) for adsorption of the 2'-deoxykanamycin A product. The resin column was then washed with water and then with 0.1N aqueous ammonia and subsequently eluted with 0.3N aqueous ammonia. The eluate was collected in 2 ml-fractions and the active fractions Nos. 6 to 10 were combined together and concentrated to dryness under reduced pressure to give 190 mg of the above titled compound. Yield 47%.

m.p. 208°~221° C. (dec.) $[\alpha]_D^{25} +124.8°$ (c 0.9, H$_2$O)

$^1$H-NMR (D$_2$O): δ5.46 (1H, d, J=3.75, 1'-H) δ5.02 (1H, d, J=3.8, 1''-H) δ2.25 (1H, q, J=4 and 10 Hz, 2' equatorial-H) δ1.72 (1H, d-t, J=3.75 and 12 Hz, 2' axial-H)

Elemental analysis Calcd. for C$_{18}$H$_{36}$N$_4$O$_{10}$.3/2H$_2$O: C: 43.61, H: 7.94, N: 11.30%; Found: C: 43.36, H: 7.50, N: 11.30%.

EXAMPLE 2

Production of 2'-epikanamycin A (1) Preparation of 1,3,6',3''-tetra-N-ethoxycarbonyl-2'-O-epi-benzoyl-3',4',2'',4'',6''-penta-O-benzoyl-kanamycin A The 1,3,6',3''-tetra-N-ethoxycarbonyl-2'-O-trifluoromethylsulfonyl-3',4',2'',4'',6''-penta-O-benzoylkanamycin A (400 mg) obtained in the above Example 1 (4) was dissolved in 10 ml of DMF and the resultant solution was admixed with 250 mg of sodium benzoate. The admixture obtained was agitated at 80° C. for 5 hours to effect the reaction of replacing the 2'-O-trifluoromethylsulfonyl group by the 2'-O-benzoyl group. The reaction mixture was distilled under reduced pressure to remove the solvent therefrom, and the residue was admixed with 20 ml of ethyl acetate and then washed twice with water. The organic layer was dried over anhydrous sodium sulfate and then concentrated to dryness under reduced pressure to give 380 mg of a crude product of the above titled compound. This was purified by chromatography with silica gel (10 g) developed with chloroform-methanol (50:1) to afford 270 mg of the titled compound. Yield 69%.

m.p. 118°~134° C. $[\alpha]_D^{23} +41.7°$ (c 0.6, CHCl$_3$)

Elemental analysis Calcd. for C$_{72}$H$_{76}$N$_4$O$_{25}$: C: 61.87, H: 5.49, N: 4.01%; Found: C: 61.66, H: 5.53, N: 3.80%.

(2) Production of 2'-epikanamycin A

The product (250 mg) of the above procedure (1) was dissolved in 5 ml of methanol and the resultant methanolic solution was admixed with 0.15 ml of a solution of 28% sodium methoxide in methanol to adjust the mixture to pH 11. The mixture was allowed to stand at ambient temperature for 30 minutes to effect the reaction for removal of the benzoyl groups. The reaction mixture was then neutralized by addition of 1N-HCl and the neutralized solution was concentrated under reduced pressure. The concentrated solution was admixed with 800 mg of barium hydroxide (Ba(OH)$_2$.8-H$_2$O) and 10 ml of water, and the whole mixture was agitated and heated for 3 hours under refluxing and stirring to effect the N-deprotecting reaction. After allowing to cool, the reaction solution was neutralized by passage of carbon dioxide gas therethrough and then filtered to remove the insoluble matter. The filtrate was passed through a column of Amberlite CG-50 (NH$_4$$^+$ form, 5 ml) for adsorption of the 2'-epikanamycin A product. The resin column was washed with water and then with 0.1N aqueous ammonia and further eluted with 0.3N aqueous ammonia. The eluate was collected in 0.7 ml-fractions and the active fractions Nos. 51 to 53 were combined together and concentrated to dryness under reduced pressure to afford 45 mg of the above titled compound.

m.p. 194°~225° C. (dec.) $[\alpha]_D^{23} +100.8°$ C. (c 0.8, H$_2$O)

Elemental analysis Calcd. for C$_{18}$H$_{36}$N$_4$O$_{11}$.H$_2$CO$_3$.5/2 H$_2$O: C: 38.57, H: 7.34, N: 9.47%; Found: C: 38.46, H: 6.97, N: 9.64%.

EXAMPLE 3

Production of 2'-epikanamycin B (1) Preparation of 1,3,6',3''-tetra-N-ethoxycarbonyl-2'-deoxy-2'-epi-azido-3',4',2'',4'',6''-penta-O-benzoylkanamycin A.

The 1,3,6',3''-tetra-N-ethoxycarbonyl-2'-O-trifluoromethylsulfonyl-3',4',2'',6''-penta-O-benzoyl-kanamycin A (1.0 g) obtained in the above Example 1 (4) was dissolved in 20 ml of DMF, and the resultant solution was admixed with 250 mg of sodium azide (NaN$_3$), followed by heating at 100° C. for 3 hours under agitation. The reaction mixture was distilled under reduced pressure, and the residue was admixed with 50 ml of ethyl acetate. The admixture obtained was washed three times with water. The organic layer was dried over anhydrous sodium sulfate and then distilled under reduced pressure to remove the solvent therefrom. A crude product of the above titled compound was obtained in a yield of 890 mg and it was then purified by chromatography with silica gel (15 g) developed with chloroform-methanol (50:1) to afford 708 mg of the titled compound. Yield 77%.

m.p. 167°~180° C. $[\alpha]_D^{24} +90.4°$ (c 0.8, CHCl$_3$)

IR($\nu_{KBR}$cm$^{-1}$): 2100 (—N$_3$) (1140, 1415 vanished SO$_2$CF$_3$)

Elemental analysis Calcd. for $C_{65}H_{71}N_7O_{23}$: C: 59.21, H: 5.44, N: 7.44%; Found: C: 58.96, H: 5.45, N: 7.38%.

(2) Production of 2'-epikanamycin B

The 2'-azido-kanamycin A derivative (500 mg) obtained in the above procedure (1) was dissolved in 12 ml of methanol, and the resultant solution was admixed with 0.3 ml of a solution of 28% sodium methoxide in methanol, followed by allowing to stand at ambient temperature for 30 minutes for the reaction of removing the benzoyl groups. The reaction solution was neutralized by addition of 1N-HCl and then acidified by addition of 0.1 ml of acetic acid, followed by addition of 30 mg of palladium black. The mixture obtained was subjected to catalytic hydrogenation with hydrogen gas at ambient temperature and under atmospheric pressure. The reaction mixture was analysed for the presence of the 2'-epi-azido-kanamycin A derivative remaining unreacted, by means of a thin layer chromatography on silica gel plate (the 2'-epi-azido-kanamycin A derivative gave Rf 0.5, while the reduction product obtained, that is, the 1,3,6',3''-tetra-N-ethoxycarbonyl-2'-deoxy-2'-epi-amino-kanamycin A gave Rf 0.24 when subjected to a silica gel thin layer chromatography developed with chloroform-methanol-concentrated aqueous ammonia (9:4:1 by volume)). The catalytic hydrogenation continued until it was confirmed by the thin layer chromatography that the 2'-epi-azido-kanamycin A derivative had been consumed entirely. The reaction mixture was then filtered to remove the catalyst, and the filtrate was concentrated under reduced pressure to remove the solvent. The residue was admixed with 1.5 g of potassium hydroxide and 10 ml of water and the admixture was heated at 100° C. for 3 hours to effect the reaction for removal of the ethoxycarbonyl groups. After allowing to cool, the reaction mixture was neutralized by addition of concentrated hydrochloric acid and then passed through a column of Amberlite CG-50 ($NH_4^+$, 10 ml) resin for adsorption of the 2'-epikanamycin B product. The resin column was washed with water and then with 0.1N aqueous ammonia and subsequently eluted with 0.3N aqueous ammonia. The eluate was collected in 1.5 ml-fractions and the active fractions Nos. 3 to 8 were combined together and concentrated to dryness under reduced pressure to give 74 mg of the titled compound.

Yield 40%.

m.p. 205°~220° C. (dec.) $[\alpha]_D^{24} + 105°$ (c 0.5, $H_2O$)

Elemental analysis Calcd. for $C_{18}H_{37}N_5O_{10} \cdot H_2CO_3$: C 41.82, H: 7.22, N: 12.84%; Found: C: 41.67, H: 7.16, N: 12.70%.

What we claim is:

1. A 2'-modified kanamycin compound of the formula (I):

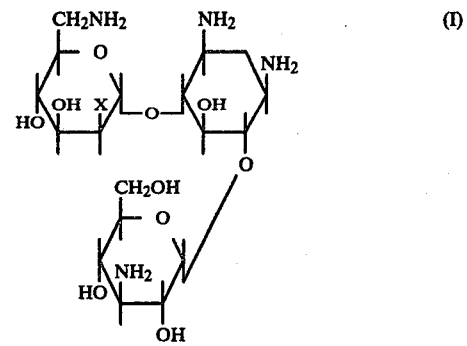

wherein X is selected from the group consisting of hydrogen, hydroxyl or amino, or a pharmaceutically acceptable acid-addition salt thereof.

2. A compound as claimed in claim 1 which is 2'-deoxykanamycin A, corresponding to the compound of the formula (I) where X is hydrogen.

3. A compound as claimed in claim 1 which is 2'-epikanamycin A, corresponding to the compound of the formula (I) where X is hydroxyl.

4. A compound as claimed in claim 1, which is 2'-epikanamycin B, corresponding to the compound of the formula (I) where X is amino.

5. A process for the production of 2'-deoxykanamycin A according to claim 2, which comprises the consecutive steps of:

(a) reacting a 1,3,6',3''-tetra-N-protected-2',3',4',2'',4'',6''-hexa-O-benzoyl or acetyl-kanamycin A of the formula (IV')

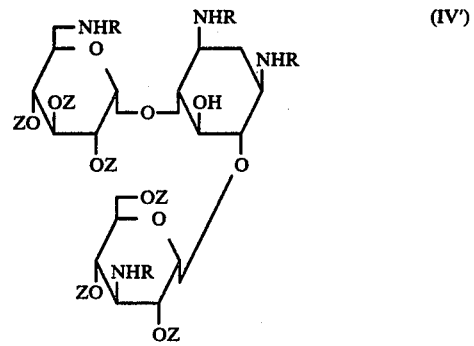

wherein R is an amino-protecting group and Z denotes benzoyl or acetyl, with hydrazine, hydrazine hydrate, methyl hydrazine or hydroxylamine in pyridine at a temperature of −10° C. to 50° C. to preferentially remove the 2'-O-benzoyl or acetyl group from the compound (IV'), (b) reacting the resultant 1,3,6',3''-tetra-N-protected-3',4',2'',4'',6''-penta-O-benzoyl or acetyl-kanamycin A with trifluoromethylsulfonyl chloride or trifluoromethanesulfonic anhydride in pyridine at a temperature of 0° C. to 30° C. to give a 1,3,6',3''-tetra-N-protected-2'-O-trifluoromethylsulfonyl-3',4',2'',4'',6''-penta-O-benzoyl or acetyl-kanamycin A of the formula (VI')

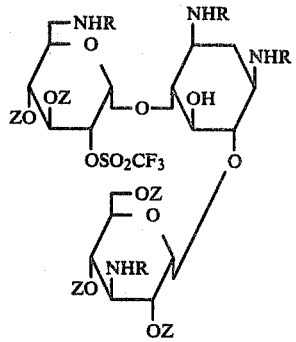

wherein R and Z are as defined above, (c) reacting the above compound (VI') with an alkali metal thiophenolate in an organic solvent at a temperature of 10° C. to 40° C. to give a 1,3,6',3"-tetra-N-protected-2'-deoxy-2'-epi-2'-phenylthio-3',4',2",4",6"-penta-O-benzoyl or acetyl-kanamycin A of the formula (VII')

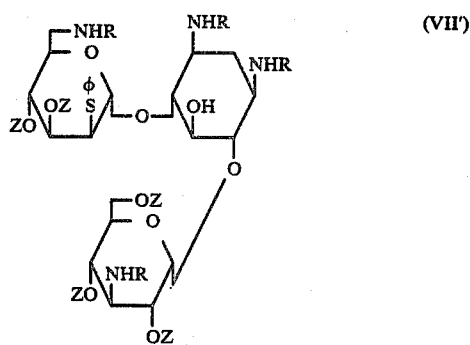

wherein R and Z are as defined above and φ denotes phenyl, (d) reacting the above compound (VII') with Ranney nickel in ethanol to remove the 2'-epi-2'-phenylthio group therefrom, (e) reacting the resultant 1,3,6',3"-tetra-N-protected-2'-deoxy-3',4',2",4",6"-penta-O-benzoyl or acetyl-kanamycin A with an alkali metal methoxide to remove the benzoyl or acetyl groups (Z) therefrom and produce the tetra-N-protected 2'-deoxy-kanamycin A compound of the formula (II')

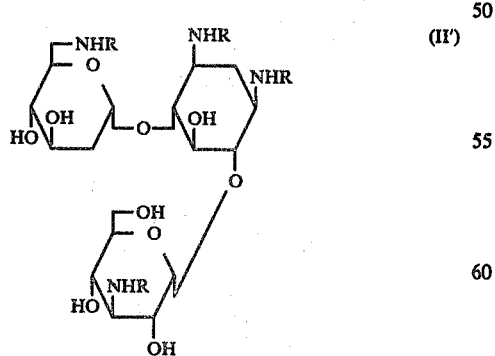

wherein R is as defined above, and (f) removing the residual amino-protecting groups (R) from the N-protected 2'-deoxykanamycin A compound (II') to produce 2'-deoxykanamycin A.

6. A process for the production of 2'-epikanamycin A which comprises the consecutive steps of:

(a) reacting a 1,3,6',3"-tetra-N-protected-2',3',4',2",4",6"-hexa-O-benzoyl or acetyl-kanamycin A of the formula (IV')

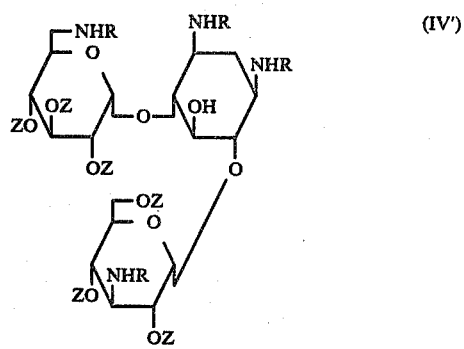

wherein R is an amino-protecting group and Z denotes benzoyl or acetyl, with hydrazine, hydrazine hydrate, methyl hydrazine or hydroxylamine in pyridine at a temperature of −10° C. to 50° C. to preferentially remove the 2'-O-benzoyl or acetyl group from the compound (IV'), (b) reacting the resultant 1,3,6',3"-tetra-N-protected-3',4',2",4",6"-penta-O-benzoyl or acetylkanamycin A with trifluoromethylsulfonyl chloride or trifluoromethanesulfonic anhydride in pyridine at a temperature of 0° C. to 30° C. to give a 1,3,6',3"-tetra-N-protected-2'-O-trifluoromethylsulfonyl-3',4',2",4",6"-penta-O-benzoyl or acetyl-kanamycin A of the formula (VI')

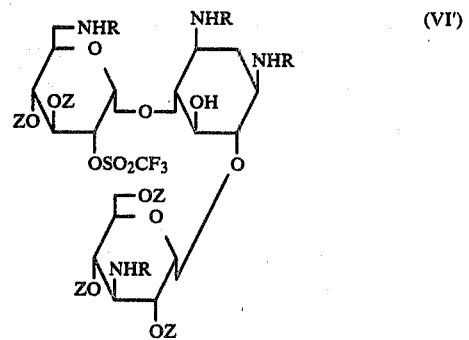

wherein R and Z are as defined above, (c) reacting the above compound (VI') with sodium or potassium benzoate or acetate in an organic solvent at a temperature of from ambient temperature to the refluxing temperature of the solvent employed, to produce a 1,3,6',3"-tetra-N-protected-2'-O-epi-benzoyl or epiacetyl-3',4',2",4",6"-penta-O-benzoyl or acetyl-kanamycin A of the formula (IX')

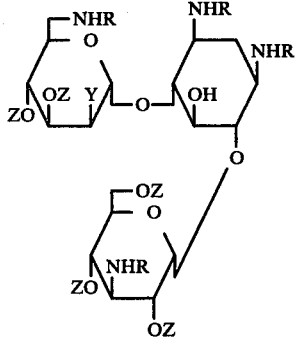

wherein R and Z are as defined above and Y denotes a benzoyl or acetyl group, (d) reacting the above compound (IX') with an alkali metal metnhoxide to remove the benzoyl or acetyl groups (Z and Y) therefrom and produce the tetra-N-protected 2'-epikanamycin A compound of the formula (II'')

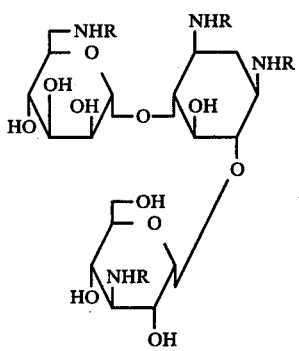

wherein R is as defined above, and (e) removing the residual amino-protecting groups (R) from the N-protected 2'-epikanamycin A compound (II'') to produce 2'-epikanamycin A.

7. A process for the production of 2'-epikanamycin B which comprises the consecutive steps of:

(a) reacting a 1,3,6',3''-tetra-N-protected-2',3',4',2'',4'',6''-hexa-O-benzoyl or acetyl-kanamycin A of the formula (IV')

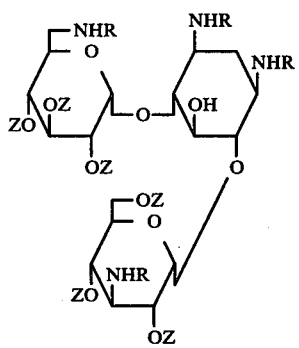

wherein R is an amino-protecting group and Z denotes benzoyl or acetyl, with hydrazine, hydrazine hydrate, methyl hydrazine or hydroxylamine in pyridine at a temperature of $-10°$ C. to $50°$ C. to preferentially remove the 2'-O-benzoyl or acetyl group from the compound (IV'), (b) reacting the resultant 1,3,6',3''-tetra-N-protected-3',4',2'',4'',6''-penta-O-benzoyl or acetyl-kanamycin A with trifluoromethylsulfonyl chloride or trifluoromethanesulfonic anhydride in pyridine at a temperature of $0°$ C. to $30°$ C. to give a 1,3,6',3''-tetra-N-protected-2'-O-trifluoromethylsulfonyl-3',4',2'',4'',6''-penta-O-benzoyl or acetyl-kanamycin A of the formula (VI')

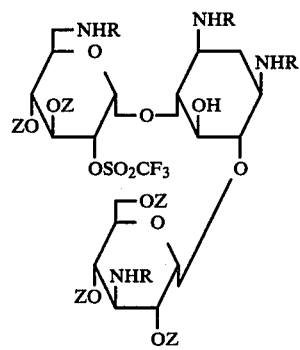

wherein R and Z are as defined above, (c) reacting the above compound (VI') with an alkali metal azide in an organic solvent at a temperature of from $50°$ C. to the refluxing temperature of the solvent employed, to produce a 1,3,6',3''-tetra-N-protected-2'-deoxy-2'-epi-azido-3',4',2'',4'',6''-penta-O-benzoyl or acetyl-kanamycin A of the formula (X')

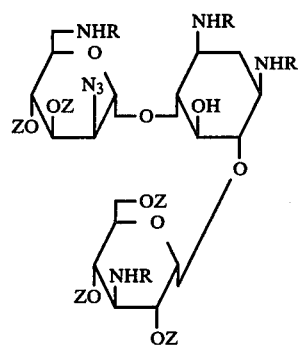

wherein R and Z are as defined above, (d) reacting the above compound (X') with an alkali metal methoxide to remove the benzoyl or acetyl groups (Z) therefrom and produce the corresponding 1,3,6',3''-tetra-N-protected-2'-deoxy-2'-epi-azidokanamycin A of the formula (XI')

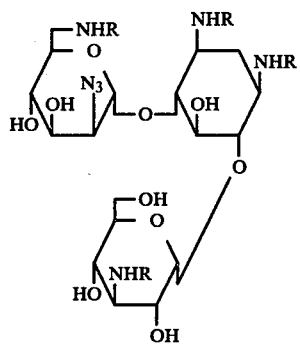

wherein R is as defined above, (e) reducing the 2'-epi-azido group of the above compound (XI') with hydrogen into the amino group and produce a 1,3,6,3''-tetra-N-protected-2'-epikanamycin B of the formula (II''')

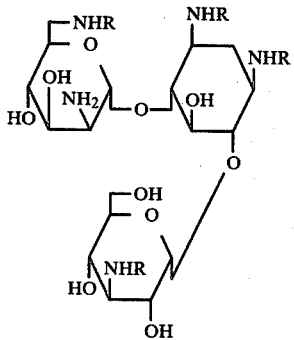

wherein R is as defined above, and (f) removing the residual amino-protecting groups (R) from the N-protected 2'-epikanamycin B compound (II''') to produce 2'-epikanamycin B.

8. An antibacterial composition comprising as the active ingredient 2'-deoxykanamycin A, 2'-epikanamycin A or 2'-epikanamycin B or a pharmaceutically acceptable acid-addition salt thereof in an antibacterially effective amount to combat bacteria, in combination with a carrier for the active ingredient compound.

9. The 1,3,6',3''-tetra-N-ethoxycarbonyl-2'-O-trifluoromethylsulfonyl-2',3',4',2'',4'',6''-penta-O-benzoyl-kanamycin A of the formula

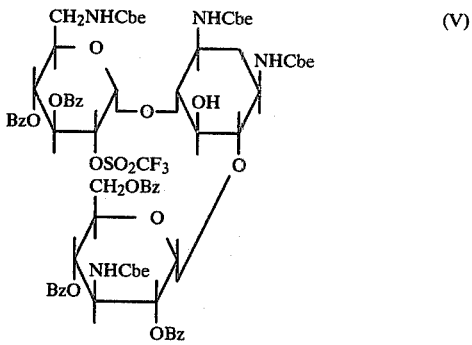

wherein Cbe denotes ethoxycarbonyl and Bz denotes benzoyl.

* * * * *